United States Patent [19]

Sedelmeier et al.

[11] Patent Number: 5,625,059

[45] Date of Patent: Apr. 29, 1997

US005625059A

[54] PROCESS FOR THE MANUFACTURE OF 4-ACETOXY-3-HYDROXYETHYL-AZETIDINONE

[75] Inventors: Gottfried Sedelmeier, Schallstadt, Germany; Jacques Bersier, Riehen, Switzerland

[73] Assignee: Ciba-Geigy Corporation, Tarrytown, N.Y.

[21] Appl. No.: 463,487

[22] Filed: Jun. 5, 1995

Related U.S. Application Data

[62] Division of Ser. No. 437,160, May 8, 1995, abandoned, which is a continuation of Ser. No. 180,723, Jan. 13, 1994, abandoned, which is a division of Ser. No. 937,457, Aug. 27, 1992, Pat. No. 5,312,914, which is a continuation of Ser. No. 732,995, Jul. 19, 1991, abandoned, which is a continuation of Ser. No. 629,096, Dec. 17, 1990, abandoned, which is a continuation of Ser. No. 445,919, Dec. 4, 1989, abandoned, which is a continuation of Ser. No. 153,694, Feb. 8, 1988, abandoned.

[30] Foreign Application Priority Data

Feb. 17, 1987 [CH] Switzerland .................. 577/87

[51] Int. Cl.$^6$ .................................................. C07D 499/00
[52] U.S. Cl. .................................................. 540/310
[58] Field of Search .............................................. 540/310

[56] References Cited

U.S. PATENT DOCUMENTS

| 4,287,123 | 9/1981 | Liu et al. | 540/200 |
|---|---|---|---|
| 4,556,514 | 12/1985 | Sunagawa et al. | 514/195 |
| 4,631,150 | 12/1986 | Battistini et al. | 540/310 |
| 4,719,207 | 1/1988 | Tamura et al. | 514/210 |
| 4,742,052 | 5/1988 | Sunagawa et al. | 514/195 |
| 4,845,210 | 7/1989 | Nakai et al. | 540/310 |
| 4,927,507 | 5/1990 | Schneider et al. | 540/200 |
| 4,952,288 | 8/1990 | Lynch et al. | 540/200 |

FOREIGN PATENT DOCUMENTS

| 0078026 | 5/1983 | European Pat. Off. |
|---|---|---|
| 0180252 | 5/1986 | European Pat. Off. |
| 0181831 | 5/1986 | European Pat. Off. |
| 902710 | 10/1985 | Germany . |
| 2042520 | 9/1980 | United Kingdom . |

OTHER PUBLICATIONS

Ben–Ishai, D et al. "A New Synthesis of a–Amino Acids–III: Amidoalkylation of Active Methylene Compound with Glyoxylic Acid Derivatives" Tetrahedron, 34: 467–473 (1978).

Kametani, T. et al. "Studies on the Synthesis of Heterocyclic Compounds 800: A Formal Total Synthesis of (±)–Thienamycin and a (±)–Decysteaminylthienamycin Derivative" Journal of the American Chemical Society 102(6) 2060–2065 (1980).

Barrett et al. "Studies on the Nactins: Total Synthesis of (±)–tert–Butyl 8-0-(tert—Butyldimethylsily)nonactate," Journal of Organic Chemistry, 48: 5017–5022 (1983).

Kopinski et al. "The Chemistry of Aryllead Tricarborylates, Synthesis of Some α–Aryl α,β–Unsaturated Carbonyl Compounds," Aust J. Chem. 36: 311–316 (1983).

Caldin, E. F. and Wolferden, J. J. "The Kinetics of the Decomposition of the γ–Bromobutyrate Ion in Neutral and in alkaline Solution", JCS Chem. Soc. 264: 1239–1241 (1936).

Maruyama et al. "A Synthesis of a Versatile Intermediate Leading to Thienamycin Analogs", Bull. Chem. Soc. Jpn. 58: 3264–3270 (1985).

Leanza et al. "An Efficient Synthesis of 2–Substituted Thio–6–Hydroxyethyl–Penem–3–Carboxylic Acids via 2–Thioxopenams", Tetrahedon, 39 (15): 2505–2513 (1983).

Reider et al. "A Total Synthesis of Thienamycin: A New Approach From Aspartic Acid", Tetrahedron Letters, 23 (22): 2293–2296 (1982).

Shiozaki et al, "Stereospecific Synthesis of Chiral Precursors of Thienamycin from L–Threonine" Tetrahedron, 40 (10): 1795, 1802 (1984).

Hanessian, S. et al. "Novel Synthetic Approaches to the Penems: Total Synthesis of Penem FCE 22101", Lectures in Heterocyclic Chemistry VIII, 43–49 (1985).

(List continued on next page.)

*Primary Examiner*—C. Warren Ivy
*Assistant Examiner*—Raymond Covington
*Attorney, Agent, or Firm*—Gregory D. Ferraro; Karen G. Kaiser

[57] ABSTRACT

The invention relates to a novel process for the manufacture of 4-acetoxy-3-hydroxyethyl-azetidinone of the formula

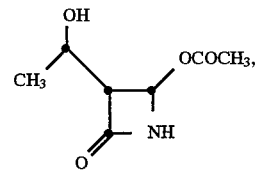

especially 4(R)-acetoxy-3(R)-(1'(R)-hydroxyethyl)-2-azetidinone, from enantiomerically pure compounds of the formula

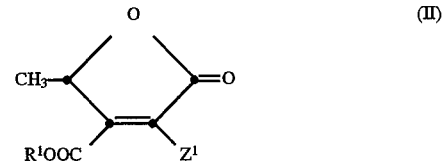

in which $R^1$ represents lower alkyl and $Z^1$ represents amino, arylmethylamino, acylamino or azido, by reduction of the C=C double bond and optionally of the arylmethylamino or azido group with hydrogen, opening of the lactone ring, cyclisation to the β-lactam, optionally after hydrolysis of the acylamino group, and oxidative decarboxylation of the original lactone carboxy group in the presence of an acetate-yielding agent. Compounds of the formula I can be used as starting materials for the manufacture of β-lactam antibiotics. The invention also relates to novel intermediates and starting materials.

1 Claim, No Drawings

OTHER PUBLICATIONS

Timori et al. "Synthetic Studies on Biologically Important Natural Products via Vinyloxyborane–Imine Condensation" Tenren Yuki Kagobutsu Toronkai Koen Yoshishu, 28: 542–549 (1986) English Abstract.

Hatanaka, M. et al. "Synthetic Studies on Thienamycin and 1β–Methyl=Carbapenem Starting from (R)–3–Hydroxybutyrate", Chem. Abstracts 108 (3): 21560w (1988).

Rossi, A. et al. "α–Keto–γ–Alkyl–γ–Lactones" Helv. Chim. Acta 31: 473–493 (1948) English Abstract.

Fleck, F. et al. "The Catalytic Hydrogenation of Enolizable α–Keto–γ–Lactones", Helv Chim Acta 33: 130–139 (1950) English Abstracts.

Schmidt, Richard et al "Preparation and Addition of Vinyl-lithium Compounds From Dimethyl Acetylenedicarboxylate Adducts," Synthesis 9: 725–727 (1983) English Abstract.

PROCESS FOR THE MANUFACTURE OF 4-ACETOXY-3-HYDROXYETHYL-AZETIDINONE

This is a divisional of Ser. No. 08/437,160, filed May 8, 1995, now abandoned, which is a continuation of Ser. No. 08/180,723, filed Jan. 13, 1994, now abandoned which is a divisional of Ser. No. 07/937,457, filed Aug. 27, 1992, now U.S. Pat. No. 5,312,914, which is a continuation of Ser. No. 732,995, filed Jul. 19, 1991, now abandoned which is a continuation of Ser. No. 629,096, filed Dec. 17, 1990, now abandoned which is a continuation of Ser. No. 07/445,919, filed Dec. 4, 1989, now abandoned which is a continuation of Ser. No. 07/153,694, filed Feb. 8, 1988, now abandoned.

The invention relates to a novel process for the manufacture of 4-acetoxy-3-hydroxyethyl-azetidinone and its diastereoisomers, which can be used as starting materials for the manufacture of β-lactam antibiotics. The invention also relates to novel intermediates and starting materials.

The 4-acetoxy-3-hydroxyethyl-azetidinone of the formula I, which can be manufactured in accordance with the process of the invention, especially the 4(R)-acetoxy-3(R)-(1'(R)-hydroxyethyl)-2-azetidinone of the formula Ia

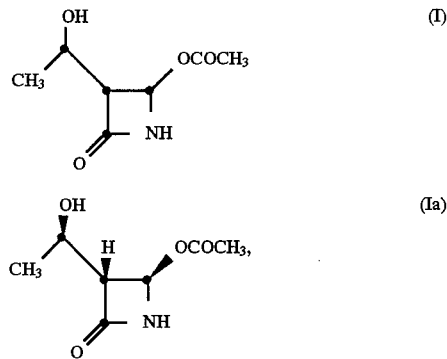

is suitable as a starting material for the manufacture of a large number of highly effective β-lactam antibiotics, for example penems, carbapenems or corresponding oxapenem, penicillin or cephalosporin derivatives. In these reactions, the acetoxy group at the 4-position of the azetidinone is exchanged for suitable sulphur or carbon nucleophiles. Such reactions are explained, for example, in a synoptical article by W. Dürckheimer et al., Angew. Chem. Int. Ed. Engl. 24, 180 (1985).

Penems are obtained, for example, by reacting the compound of formula I, optionally after introducing a protecting group at the hydroxy group and/or at the lactam nitrogen atom, with a mercaptan, a thio acid, a dithio acid, a trithiocarbonate or a related compound, alkylating the nitrogen atom with a suitable acetic acid derivative and finally closing the sulphur-containing five-membered ring. In order to synthesise carbapenems, for example, the compound of formula I or a protected derivative of that compound is reacted with a suitably substituted enol silyl ether, tin enolate, boron enolate, tetraallyltin or a related compound, and the resulting products are further processed accordingly.

Essential criteria for the antibiotic activity of penems and carbapenems are not only the nature and the position, but also the spatial configuration, of the substituents. The diastereoisomer of formula Ia has a spatial configuration of the hydroxy, hydroxyethyl and acetoxy groups favouring its use as a starting material for antibiotically active β-lactam antibiotics. Other diastereoisomers, too, however, are suitable for the further processing: In a substitution reaction with sulphur and carbon nucleophiles under suitable reaction conditions, the cis-compound epimeric at C(4) also yields the trans configuration of the substituents at the azetidinone ring already present in the compound of formula Ia. The (S)-hydroxyethyl compound epimeric at C(1') can be used because at a later stage conversion into an (R)-hydroxyethyl compound can be achieved by substitution with inversion.

The manufacture of the compound of formula I is known. EP 78026 and Tetrahedron Letters 23, 2293–2296 (1982), for example, describe a process in which the compound of formula Ia is manufactured from L-aspartic acid by acylation or hydroxyalkylation of the dianion of an N-protected azetidinone-4-carboxylic acid. EP 106652 describes a process in which a Schiff's base of glyoxylic acid is reacted with diketene, the acetyl group in the side chain is reduced to hydroxyethyl, and the enantiomers are separated by way of diastereoisomeric esters. In EP 171064, a process is described in which a 4-ethynyl-azetidinone is synthesised by cycloaddition and, subsequently, the ethynyl radical is converted into acetyl and finally, by Baeyer-Villiger reaction, into acetoxy. EP 181831 describes a process in which an α,β-epoxybutyryl-acetonylamide is cyclised with a base and the 3-hydroxyethyl-4-acetylazetidinone formed is oxidised to the 4-acetoxy compound.

DESCRIPTION OF THE PROCESS

The invention relates to a process for the manufacture of diastereoisomerically pure compounds of the formula

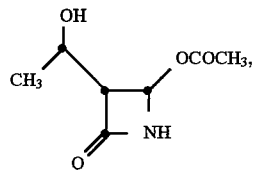

especially the (3R,4R,1'R)-diastereoisomer of formula Ia, which process is characterised in that an enantiomerically pure compound of the formula

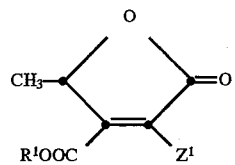

in which $R^1$ represents lower alkyl and $Z^1$ represents amino, arylmethylamino, acylamino or azido, or a salt thereof, is reduced with hydrogen and, if desired, an acylamino group $Z^1$ and/or the lower alkoxycarbonyl group $COOR^1$ is(are) hydrolysed, in a resulting compound of the formula

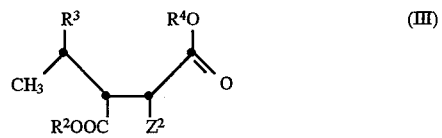

in which $R^2$ represents hydrogen or lower alkyl, $R^3$ and $R^4$ together represent a bond and $Z^2$ represents amino or acylamino, or in a salt thereof, if desired after conversion of the radicals $R^2$ and $Z^2$ and/or after conversion of diastereoisomers one into another, the lactone ring is opened with a base and, if $Z^2$ represents acylamino, the acylamino group $Z^2$ is hydrolysed, in a resulting compound of the formula III in which $R^2$ represents hydrogen or lower alkyl, $R^3$ represents hydroxy, R⁴ represents hydrogen and Z² represents amino, or in a salt thereof, R³ and COOR⁴ and, if R² represents hydrogen, also COOR², are protected by a protecting group, the β-lactam ring is closed with a strong base and the protecting groups are removed, and a resulting compound of the formula

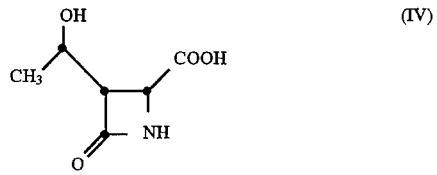

or a salt thereof is oxidatively decarboxylated in the presence of an acetate-yielding agent.

Compared with the known processes, the novel process according to the invention has important advantages: with this process the compound of formula I and the diastereoisomers thereof can be produced in a high total yield, with high stereoselectivity, few reaction steps and simple, inexpensive reagents. Surprisingly it is possible, starting from enantiomerically pure compounds of the formula II having only one chiral carbon atom, to obtain pure diastereoisomers of the formula III having three chiral carbon atoms by selection of the reduction conditions and also by subsequent isomerisation where appropriate. It is also surprising that the reaction sequence for producing the compound I, which contains sensitive functional groups, requires a protecting group only for the formation of the β-lactam ring, at which stage it can be introduced and removed again easily in situ. The fact that pure diastereoisomers of the formula I can be obtained in few reaction steps from a starting material of the formula II is also surprising when it is taken into account that this starting material is simple to synthesise from inexpensive enantiomerically pure natural products or can be obtained by enantiomeric separation of synthetic racemic material.

The general terms and names used in defining substituents have, preferably, the following meanings:

"Lower", for example in lower alkyl, lower alkoxy or lower alkanoyl, means that the radicals and groups so designated contain from 1 to 7 carbon atoms and, preferably, from 1 to 4 carbon atoms.

Lower alkyl R¹ or R² has preferably from 1 to 7 carbon atoms and is, for example, methyl, ethyl, n-propyl, isopropyl, n-butyl or tert-butyl.

Arylmethylamino Z¹ is, for example, benzylamino, dibenzylamino, 2-, 3- or 4-methylbenzylamino, α- or β-naphthylmethylamino or diphenylmethylamino.

Acylamino Z¹ or Z² is, for example, unsubstituted or substituted lower alkanoylamino, for example formylamino, acetylamino, propionylamino, tert-butylcarbonylamino, chloroacetylamino, trichloroacetylamino or trifluoroacetylamino, lower alkoxycarbonylamino, for example tert-butoxycarbonylamino, aryl-lower alkoxycarbonylamino, for example benzyloxycarbonylamino, 4-nitrobenzyloxycarbonylamino or diphenylmethoxycarbonylamino, or arylcarbonylamino, for example benzoylamino.

A carboxy-protecting group R² or R⁴ or the protecting group of protected hydroxy R³ is, for example, one of the protecting groups as described in standard works, for example in J. F. W. McOmie, "Protective Groups in Organic Chemistry", Plenum Press, London and New York 1973, in Th. W. Greene, "Protective Groups in Organic Synthesis", Wiley, New York 1981, in "The Peptides", vol. 3 (edited by E. Gross and J. Meienhofer), Academic Press, London and New York 1981, and in "Methoden der organischen Chemie", Houben-Weyl, 4th edition, vol. 15/I, Georg Thieme Verlag, Stuttgart 1974.

Preferred protecting groups are, for example, those groups that can be introduced at the hydroxy group and the carboxy group(s) simultaneously, that protect the said functional groups against reacting with non-nucleophilic or only slightly nucleophilic basic reagents, and that can be removed again by hydrolysis under mild conditions. Suitable carboxy-protecting groups R² or R⁴ are especially tri-lower alkylsilyl radicals, for example trimethylsilyl, tributylsilyl, triisopropylsilyl, tert-butyl-dimethyl-silyl or 1,1,2-trimethylpropyl-dimethyl-silyl, preferably trimethylsilyl, but also aryl-substituted silyl radicals, for example dimethylphenyl-silyl or triphenylsilyl. Also preferred are lower alkyl radicals that are substituted and/or branched in the 1-position, for example tert-lower alkyl, for example tert-butyl, di- or tri-arylmethyl, for example diphenylmethyl, di(p-methoxyphenyl)methyl or trityl, lower alkoxy-lower alkyl, for example methoxymethyl, 1-methoxyethyl or 1-ethoxyethyl, or lower alkylthio-lower alkyl, for example methylthiomethyl or 1-ethylthioethyl, and also the corresponding cyclic groups 2-oxa- or 2-thia-cycloalkyl having from 5 to 7 ring atoms, for example 2-tetrahydrofuryl or 2-tetrahydropyranyl.

Protected hydroxy R³ is preferably an -oxy radical corresponding to the above definition of R² and R⁴, for example tri-lower alkylsilyloxy, for example trimethylsilyloxy, aryl-substituted silyloxy, for example triphenylsilyloxy, lower alkoxy that is substituted and/or branched in the 1-position, for example tert-butoxy or methoxymethoxy, or 2-oxa- or 2-thia-cycloalkoxy, for example 2-tetrahydropyranyloxy.

Salts are, for example, acid addition salts of the amino group in compounds of the formula II or III, for example with inorganic acids, for example hydrochloric acid, sulphuric acid, nitric acid or phosphoric acid, or with organic carboxylic or sulphonic acids, for example acetic acid, chloroacetic acid, trichloroacetic acid, trifluoroacetic acid, propionic acid, glycolic acid, fumaric acid, benzoic acid, methanesulphonic acid, trifluoromethanesulphonic acid, ethanesulphonic acid, camphor-10-sulphonic acid, benzenesulphonic acid, toluenesulphonic acid, 4-nitrobenzenesulphonic acid, 2,4-dinitrobenzenesulphonic acid or naphthalene-2-sulphonic acid.

Carboxylic acids of the formulae III and IV may form alkali metal salts, for example sodium or potassium salts, or also alkaline earth metal salts, for example magnesium or calcium salts, heavy metal salts, for example copper, lead or zinc salts, ammonium salts, salts with organic amines, for example with optionally substituted mono-, di- or tri-alkylamines, for example cyclohexylamine, diethylamine, cyclohexylethylamine, dibutylamine, trimethylamine, triethylamine or tri-(2-hydroxyethyl)-amine, or with tetra-substituted organic ammonium ions, for example tetramethylammonium, tetraethylammonium or tetrabutylammonium.

Compounds of the formula III in which R² represents hydrogen and/or R⁴ represents hydrogen and Z² represents amino may also form internal salts.

The compound of formula I has three chiral carbon atoms that are independent of one another, that is carbon atoms 3 and 4 of the β-lactam ring and carbon atom 1', carrying the hydroxy group, of the hydroxyethyl side chain. Consequently, the formula I representation includes eight diastereoisomeric compounds.

The process according to the invention concerns the manufacture of all of these diastereoisomeric compounds in pure form. The manufacture of the (3R,4S,1'R)- and the (3R,4R,1'R)-diastereoisomers of formula I, especially the (3R,4R,1'R)-diastereoisomer of formula Ia, from the (R)-enantiomer of the compound of formula II, is especially preferred.

In the context of the present description, "enantiomerically pure" or "diastereoisomerically pure" indicates that the enantiomer or diastereoisomer so defined is present in an amount of at least 80% in admixture with the other enantiomer or the other diastereoisomers, respectively. This high proportion of the one stereoisomer means that it is possible, by simple physical separating methods, for example by recrystallisation of a compound according to the invention, of a suitable salt or of a suitable derivative thereof, for the proportion of that stereoisomer to be increased to, for example, more than 95%, or to be increased to such an extent that the other stereoisomers can no longer be detected by conventional analytical methods.

Compounds of the formula II in which $Z^1$ represents amino, arylmethylamino or acylamino are in equilibrium with the tautomeric form of the formula

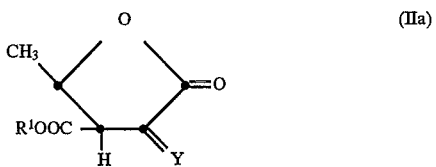

(IIa)

in which Y represents imino, arylmethylimino or acylimino. The tautomeric equilibrium depends on the nature of the substituents $R^1$ and $Z^1/Y$ and the physical conditions, for example state of aggregation, solvent, pH, pressure and temperature and this equilibrium may be frozen in the crystalline state either as depicted in formula II or in formula IIa.

Hereinafter, the designation "compound of the formula II" also includes the tautomeric form of the formula IIa.

Process steps

The reduction of a compound of formula II in which $Z^1$ represents amino, arylmethylamino, acylamino or azido, or of a salt thereof, can be carried out with hydrogen in the presence of one of the customary hydrogenation catalysts.

Such hydrogenation catalysts that are suitable for the reduction are preferably noble metal catalysts, for example platinum, palladium, ruthenium or rhodium, in finely divided metallic form, for example applied to an inert carrier having a large surface area, for example to activated carbon, Alox, barium sulphate or other alkaline earth metal salts. The noble metal hydrogenation catalysts suitable especially for the reduction of C=C double bonds, for example platinum as obtained by reducing platinum oxide with hydrogen, palladium-on-carbon, rhodium-on-Alox, or a platinum/rhodium alloy according to Nishimura, are preferred. Other suitable hydrogenation catalysts are nickel, for example Raney nickel as formed by decomposing a nickel/aluminium alloy with alkali, and also soluble noble metal complex catalysts, for example rhodium/phosphine complexes or iridium/phosphine complexes.

The hydrogenations are carried out in an inert solvent, for example in an alcohol, for example methanol, ethanol or isopropanol, in alcohol/water mixtures, for example aqueous ethanol, it being possible for the alcohol also to contain a mineral acid, for example hydrochloric acid, in a carboxylic acid, for example acetic acid or propionic acid, and also aqueous acetic acid, in a polar ester, for example ethyl acetate, in a hydrocarbon, for example toluene or cyclohexane, or in a halogenated hydrocarbon, for example methylene chloride. Preferably, the hydrogenations are carried out in a temperature range of from 0° C. to 100° C., for example at room temperature or a slightly elevated temperature of up to approximately 80° C., and at normal pressure, a slightly elevated hydrogen pressure of up to approximately 5 bars, or a high hydrogen pressure of up to approximately 100 bars depending on the substituent $Z^1$ and on the catalyst chosen. For example, with palladium-on-carbon hydrogenation is carried out preferably at from 1 to 5 bars, and with platinum, rhodium or platinum/rhodium alloy it is carried out at elevated pressure, preferably at from 50 to 100 bars.

If a compound in which $Z^1$ represents arylmethylamino or azido is hydrogenated, the reaction can be carried out in one stage, or in two stages by way of the corresponding compound of formula II in which $Z^1$ represents amino, because an arylmethylamino group and an azido group can be hydrogenated more readily than the C=C carbon double bond. Preferably, the arylmethylamino group, for example benzylamino, or the azido group, is selectively hydrogenated in the presence of palladium-on-carbon at room temperature or slightly elevated temperature, at a hydrogen pressure of from 1 to 5 bars, preferably normal pressure, in one of the solvents mentioned, for example in hydrochloric acid/ethanol or in ethyl acetate.

A compound of formula II in which $Z^1$ represents amino, or a salt thereof, can be hydrogenated directly to a compound of formula III. On the other hand, the amino group can alternatively be converted into an acylamino group $Z^1$ before the hydrogenation. The acylation is carried out under customary reaction conditions, for example using the acid anhydride or acid halide, for example acid chloride, that corresponds to the acyl group, optionally with the addition of an acid, for example p-toluenesulphonic acid, or a base, for example a tertiary amine, for example triethylamine, dimethylbenzylamine or N-methylmorpholine, an amidine, for example 1,5-diazabicyclo[4.3.0]-non-5-ene or 1,8-diazabicyclo[5.4.0]undec-7-ene, a pyridine base, for example pyridine or lutidine, or an alkali metal or alkaline earth metal carbonate, for example sodium, potassium or calcium carbonate, in an excess of the acylation agent or in an inert solvent, for example in an ether, for example diethyl ether, tetrahydrofuran or dioxan, a halogenated hydrocarbon, for example methylene chloride, an ester, for example ethyl acetate, an amide, for example dimethylformamide or N-methylpyrrolidone, or in a nitrile, for example acetonitrile, at temperatures of from −20° C. to the boiling point of the solvent, preferably from 0° C. to 50° C.

After the reduction of a compound of formula II in which $Z^1$ represents acylamino, if desired the acylamino group can be converted into a corresponding amino group. The hydrolysis is effected under customary conditions, for example with an acid or base.

Suitable acids are, for example, mineral acids, for example hydrochloric acid, sulphuric acid or phosphoric acid, or strong organic acids, for example alkanesulphonic or arenesulphonic acids, for example methanesulphonic acid, trifluoromethanesulphonic acid, benzenesulphonic acid, p-toluenesulphonic acid or p-nitrobenzenesulphonic acid, preferably in aqueous solution, for example in water or in mixtures of water and organic solvents, for example methanol, ethanol, dioxane or acetonitrile, at temperatures of from 20° C. to 150° C., preferably from 50° C. to 100° C. If $R^3$ represents hydroxy and $R^4$ represents hydrogen, then these are simultaneously removed under the mentioned acidic conditions, whereupon a bond is formed.

Suitable bases are metal hydroxides, for example alkali metal hydroxides, for example lithium, sodium or potassium hydroxide, alkali metal carbonates for example sodium or potassium carbonate, or tetra-substituted ammonium hydroxides, for example benzyltrimethylammonium hydroxide, preferably in water or one of the above-mentioned mixtures of water and organic solvents, at temperatures of from 20° C. to 120° C., for example approximately 50° C. Hydrogen peroxide, for example in the form of a 30% aqueous solution, can be added to accelerate the basic hydrolysis. During the basic hydrolysis, the lactone ring is simultaneously opened and a compound of formula III is obtained in which $R^3$ represents hydroxy and $R^4$ represents hydrogen. These radicals $R^3$ and $R^4$ can be removed again by treatment with an acid, for example with one of the above-mentioned acids, whereupon a bond is formed.

The above-mentioned acidic or basic hydrolysis conditions for an acylamino group $Z^1$ also usually cause hydrolysis of the lower alkyl ester group $COOR^1$ at the same time, so that compounds of the formula III are formed in which $R^2$ represents hydrogen. If, after hydrogenation of a compound of formula II, the lower alkyl ester group $COOR^1$ is to be hydrolysed selectively, then even milder reaction conditions will suffice. The ester is cleaved, for example, with the above-mentioned acids and bases in aqueous solution at reduced temperatures, for example from 0° C. to room temperature. It is also possible to use strong organic carboxylic acids, for example chloroacetic, trichloroacetic or trifluoroacetic acid, or organic amines, for example trialkylamines, for example triethylamine or tributylamine, or pyridine, in aqueous solution.

If, in the next step, a compound of formula III in which $R^2$ is hydrogen and $R^3$ and $R^4$ together represent a bond is to be converted into a corresponding compound in which $R^2$ represents lower alkyl, then customary esterification conditions are employed for that purpose. Suitable conditions are, for example, an excess of the corresponding lower alkanol $R^2OH$ in the presence of an acid, for example a mineral acid that is as far as possible anhydrous, for example hydrochloric acid, concentrated sulphuric acid, polyphosphoric acid or phosphorus pentoxide, an organic sulphonic acid, for example p-toluenesulphonic acid, an acidic ion exchanger or a Lewis acid, for example boron trifluoride etherate, optionally in the presence of a water-removing agent, for example a molecular sieve, or with the removal of the water of reaction by azeotropic distillation, for example with a halogenated hydrocarbon, for example methylene chloride, chloroform or carbon tetrachloride, or an aromatic hydrocarbon, for example benzene or toluene. The acidic esterification is carried out, for example, at temperatures of from 0° C. to the boiling point of the alcohol $R^2OH$ or of the azeotrope with the mentioned entraining solvent. Esterification can also be achieved with an alkylation agent, for example with diazomethane in ethereal solution.

To convert a compound of formula III in which $Z^2$ is amino and $R^3$ and $R^4$ together represent a bond into a corresponding compound in which $Z^2$ represents acylamino, the acylation conditions mentioned hereinbefore for compounds of formula II are used. Equally, the hydrolysis conditions mentioned hereinbefore can be used if, in a compound of formula III, $Z^2$ representing acylamino is to be converted into $Z^2$ representing amino and/or if $R^2$ representing lower alkyl is to be converted into $R^2$ representing hydrogen.

In a compound of formula III in which $R^2$ is lower alkyl and $R^3$ and $R^4$ together represent a bond, it is possible by means of suitable bases to achieve a conversion of pure diastereoisomers or of diastereoisomeric mixtures into diastereoisomers in which all the substituents $CH_3$, $COOR^2$ and $Z^2$ at the 5-membered lactone ring are in the trans form. Depending on the configuration of the carbon atom C(4) carrying the methyl group, predetermined by the choice of the enantiomerically pure starting material of formula II, this conversion results in the (2S,3S,4R)- or the (2R,3R,4S)-diastereoisomer. Bases suitable for such an isomerisation are, for example, tertiary amines, for example triethylamine or tributylamine, pyridine or pyridine derivatives, for example lutidine, amidine bases, for example 1,5-diazabicyclo[4.3.0]non-5-ene or 1,8-diazabicyclo[5.4.0] undec-7-ene, or basic alkaline earth metal salts, for example sodium or potassium carbonate or potassium fluoride. The isomerisation is carried out preferably in polar, anhydrous solvents, for example methanol, ethanol, tetrahydrofuran, dioxane, acetonitrile, dimethylformamide or dimethyl sulphoxide, at temperatures of from 0° C. to 50° C., for example at approximately room temperature.

In the next step, in a compound of formula III in which $R^3$ and $R^4$ together represent a bond, the lactone ring is opened by treatment with an aqueous base, for example an aqueous alkali metal hydroxide, for example lithium, sodium or potassium hydroxide, or an alkali metal carbonate, for example sodium or potassium carbonate, if desired in the presence of a solubilising organic solvent, for example methanol, ethanol or ethylene glycol, preferably at temperatures of from 0° C. to room temperature. It is also possible to apply the basic reaction conditions indicated hereinbefore under the hydrolysis of the acylamino group $Z^2$. The salt, for example an alkali metal salt, of the compound of formula III in which $R^3$ represents hydroxy and $R^4$ represents hydrogen, formed by the base treatment, is acidified with an equimolar amount of a proton-yielding acid, for example a mineral acid, for example hydrochloric acid. If $Z^2$ represents acylamino, then simultaneously with, or subsequently to, the opening of the lactone ring with an aqueous base, also the acylamino group $Z^2$ should be hydrolysed in the manner indicated hereinbefore.

In the next step, in the compound of formula III the hydroxy group $R^3$, the carboxy group $COOR^4$ and, if $R^2$ is hydrogen, also the carboxy group $COOR^2$, are protected by suitable protecting groups. The introduction and removal of the protecting groups are described in the above-cited standard works relating to protecting groups.

A silyl protecting group, for example trimethylsilyl, is introduced by means of the corresponding silyl halide, for example iodide, bromide or, preferably, chloride, in the presence of a base, for example pyridine, dimethylaminopyridine, imidazole, triethylamine, dicyclohexylamine or di(trimethylsilyl)amine, by way of the corresponding silyl amide, for example trimethylsilylacetamide or 3-(trimethylsilyl)-2-oxazolidinone, or with other reactive silyl derivatives. The corresponding halides in the presence of the mentioned bases are also suitable for the introduction of tert-lower alkyl, diarylmethyl, triarylmethyl, lower alkoxymethyl or lower alkylthiomethyl protecting groups. Tert-lower alkyl groups, and radicals substituted in the 1-position by oxygen or sulphur are introduced preferably by way of the corresponding olefins, for example isobutylene, ethyl vinyl ether, 2,3-dihydrofuran or 3,4-dihydro-2H-pyran, in the presence of an anhydrous acid, for example a mineral acid, for example hydrogen chloride, a sulphonic acid, for example p-toluenesulphonic acid, or a Lewis acid, for example boron trifluoride etherate. For the introduction of a protecting group preferably anhydrous inert solvents are used, for example hydrocarbons, for example toluene, halogenated hydrocarbons, for example methylene chloride, or ethers, for example diethyl ether or tetrahydrofuran, at temperatures of from 0° C. to the boiling point of the solvent, for example at approximately room temperature. To avoid reaction of the amino group with the reagent introducing the protecting group, the reaction should be carried out under controlled conditions, for example with equivalent amounts of the reagent, and/or then the amino group should be freed again, for example by reaction with ammonia or a primary amine, for example methylamine.

The compound of formula III in which $R^3$ represents protected hydroxy, $COOR^4$ represents protected carboxy and $COOR^2$ represents lower alkoxycarbonyl or protected carboxy, is cyclised with a strong base to form a β-lactam. Suitable strong bases are those that deprotonate preferentially the amino function without at the same time modifying the protected carboxy group(s) and, if applicable, lower alkoxycarbonyl $COOR^2$. There are suitable, for example, non-nucleophilic alkali metal amides, for example lithium diisopropylamide, lithium cyclohexylethylamide, lithium 2,2,6,6-tetramethylpiperidide or potassium bis (trimethylsilyl)amide, or lower alkyllithium or lower alkylmagnesium compounds branched in the 1-position, for example tert-butyllithium, isopropylmagnesium halide or, preferably, tert-butylmagnesium halide, for example tert-butylmagnesium chloride, in an inert solvent, for example an ether, for example diethyl ether or tetrahydrofuran, a hydrocarbon, for example toluene, pentane, hexane or cyclohexane, or a mixture of the said solvents, at temperatures of from –80° C. to room temperature, for example at approximately 0° C.

The reaction mixture is worked up in weakly acidic aqueous solution at a pH of from 2 to 5, for example in a dilute aqueous, if desired buffered, mineral acid, for example phosphoric acid, a carboxylic acid, for example acetic acid, or in a weakly acidic salt solution, for example potassium hydrogen sulphate or potassium or sodium hydrogen tartrate, the hydroxy- and carboxy-protecting groups simultaneously being removed.

The compound of formula IV obtained in this manner is oxidatively decarboxylated by lead tetraacetate or, preferably, electrochemically in the presence of an acetate-yielding agent.

For the chemical oxidative decarboxylation, the compound of formula IV is reacted with an equimolar amount or an excess of lead tetraacetate, preferably with from 1 to 1.5 equivalents, in an inert polar solvent at temperatures of from 20° C. to 80° C., for example at approximately 50° C., for example in acetic acid, dimethylformamide, N-methylpyrrolidone, hexamethylphosphoric acid triamide, tetrahydrofuran, dioxane or the like, preferably in a mixture of solvents, for example acetic acid/dimethylformamide, and, for example, with the addition of an alkali metal acetate, for example sodium or potassium acetate, and/or an amine, for example pyridine or lutidine.

For the electrochemical oxidative decarboxylation, a mono-cell or a divided cell with a mechanical diaphragm, for example of porous clay or glass or of polyvinyl chloride, or with an ion exchanger diaphragm, for example as available under the trade name Nafion®, and with electrodes made of noble metal, for example platinum, titanium alloys, for example titanium/iridium or titanium/tantalum, or also nickel, lead dioxide, glass carbon and/or graphite, is used. The electrochemical decarboxylation is carried out in the presence of an acetate-yielding agent, for example in acetic acid or a mixture of acetic acid and an inert organic solvent, for example acetonitrile, dioxane or dimethylformamide, there being added an amine, for example tri-lower alkylamine, for example triethylamine or tri-n-butylamine, or pyridine, and/or an alkali metal acetate, for example sodium or potassium acetate and, if desired, an additional conducting salt, for example a lithium, sodium, potassium or tetraalkylammonium salt, for example the corresponding tetrafluoroborate. Suitable current densities for the electrolysis are from 10 to 400 mA/cm$^2$, for example approximately 40 mA/cm$^2$. The reaction temperature is from 0° C. to 50° C., preferably from room temperature to 30° C.

Both the oxidative decarboxylation with lead tetraacetate and the electrochemical decarboxylation in the presence of an acetate-yielding agent yield preferentially a compound of formula I in which the hydroxyethyl group at C(3) and the acetoxy group at C(4) are arranged in trans position with respect to one another, that is to say yield a diastereoisomer with a (3R,4R)- or (3S,4S)-configuration.

Salts of the mentioned compounds are obtained in customary manner. Acid addition salts of the amino group in compounds of formula II or III are formed, for example, by treatment with an acid or a suitable anion exchange reagent, preferably stoichiometric amounts or only a small excess of the salt-forming agent being used. Internal salts, for example of compounds of formula III, that contain a free carboxy group can be formed, for example, by neutralising salts, such as acid addition salts, to the isoelectric point, for example with bases, or by treatment with ion exchangers or epoxides, for example propylene oxide. Salts of compounds of formula III or IV having carboxy groups can be formed, for example, by treatment with metal compounds, such as alkali metal salts of suitable organic carboxylic acids, for example the sodium salt of 2-ethylhexanoic acid, with inorganic alkali metal or alkaline earth metal salts, for example sodium hydrogen carbonate, a stoichiometric amount or a small excess of an alkali metal hydroxide, for example lithium, sodium or potassium hydroxide, or with ammonia or a suitable organic amine.

Salts can be converted in customary manner into the free compounds: metal and ammonium salts, for example, by treatment with suitable acids, and acid addition salts, for example, by treatment with a suitable basic agent.

The process of the invention also includes those forms in which intermediates are isolated and the remaining process steps are carried out with these, starting materials and reagents are manufactured in situ, and/or intermediates and end products are further processed without being isolated.

The invention relates especially also to the novel process steps mentioned hereinafter under the mentioned preferred reaction conditions, as such or as a part of a complete process for the manufacture of compounds of the formula I.

Preferred is a process for the manufacture of compounds of the formula I which is characterised in that a compound of formula IV or a salt thereof is oxidatively decarboxylated electrochemically in the presence of acetic acid and/or an alkali metal acetate, for example sodium or potassium acetate, at current densities of from 10 to 400 mA/cm$^2$ and temperatures of from 0° C. to 50° C.

More especially preferred is the mentioned process step for the manufacture of a compound of formula Ia from the (3S,4S,1'R)-diastereoisomer of the compound of formula IV.

Also preferred is a process for the manufacture of compounds of the formula IV and salts of those compounds which is characterised in that a compound of formula III in which $R^2$ represents lower alkyl, $R^3$ represents hydroxy, $R^4$ represents hydrogen and $Z^2$ represents amino, or a salt thereof, is reacted with a tri-lower alkylsilylation agent, for example trimethylsilyl chloride, in the presence of a base, for example an amine, for example hexamethyldisilazane, in an inert solvent, the resulting compound of formula III in which $R^2$ represents lower alkyl, $R^3$ represents tri-lower alkylsilyloxy, $R^4$ represents tri-lower alkylsilyl and $Z^2$ respresents amino is cyclised with a strong base, for example a non-nucleophilic alkali metal amide or a lower alkyllithium or lower alkylmagnesium compound branched in the 1-position, for example tert-butylmagnesium halide, in an inert solvent at temperature of from −80° C. to room temperature, and the resulting compound is huydrolysed and, if desired, a resulting salt is converted into the free compound or into a different salt or a resulting free compound is converted into a salt.

More especially preferred is the mentioned partial process for the manufacture of the (3S,4S,1′R)-diastereoisomer of the compound of formula IV and salts of that compound from the corresponding (2S,3S,4R)-diastereoisomer of the compound of formula III.

Also preferred is a process for the manufacture of compounds of the formula III in which $R^2$ represents lower alkyl, $R^3$ and $R^4$ together represent a bond and $Z^2$ represents amino or acylamino, and salts of these compounds, which is characterised in that a compound of formula II in which $R^1$ represents lower alkyl and $Z^1$ represents amino, arylmethylamino, acylamino or azido, or a salt thereof, is reduced with hydrogen in the presence of a noble metal catalyst, for example a platinum, palladium or platinum/rhodium catalyst, in an inert solvent, at temperatures of from 0° C. to 100° C. and a hydrogen pressure of from 1 to 100 bars and, if desired, a resulting diastereoisomeric mixture is converted with a base, for example a teritary amine or amidine, in an anhydrous polar solvent, at temperatures of from 0° C. to 50° C., into the diastereoisomer in which all of the substituents are in trans form, and, if desired, a resulting salt is converted into the free compound or into a different salt or a resulting free compound is converted into a salt.

More especially preferred is the mentioned partial process for the manufacture of the (2S,3S,4R)-, (2R,3R,4S)-, (2R,3S,4S)-, (2S,3R,4R)-, (2R,3S,4R)- and (2S,3R,4S)-diastereoisomers of the compounds of formula III, and salts of these compounds, from pure (R)- or (S)-enantiomers of the compounds of formula II.

The invention relates especially to the processes described in the Examples.

Further processing

The compound of formula I and especially the pure diastereoisomer of formula Ia can be converted according to one of the many processes known in the state of the art into valuable end products. Most of these processes require for this purpose a derivative of the compound of formula I in which the hydroxy group and/or the β-lactam nitrogen atom are protected by a protecting group. Such protecting groups can easily be introduced, for exmaple in a manner described in one of the above-mentioned synoptical works relating to protecting groups.

Advantageously, however, the compound of formula I and its diastereoisomers are further processed without protecting goups in order to avoid additional reaction steps. For example, the compound of formula Ia can, as described in European Patent Application No. 215 739, be reacted with the α-aminothiocarboxylic acid N-allyloxycarbonylthioglycine, which is protected at the nitrogen atom, and can be further processed in a few steps to the highly effective antibiotic (5R,6S,1′R)-2-aminomethyl-6-(1′-hydroxyethyl)-2-penem-3-carboxylic acid. The valuable properties of the said end product and its use are described, for example, in German Patent Application DE 34 31 980.

Intermediates

The invention also relates to novel intermediates.

The invention relates especially to compounds of the formula III in which $R^2$ represents hydrogen, lower alkyl, for example methyl or ethyl, or a carboxy-protecting group, for example trii-lower alkylsilyl, for example trimethylsilyl, tert-butyl-dimethyl-silyl or 1,1,2-trimethyulpropyl-dimethyl-silyl, aryl-substituted silyl, for example dimethylphenylsilyl or triphenylsilyl, lower alkyl substituted and/or branched in the 1-position, for example tert-butyl, diphenylmethyl, di(p-methoxyphenyl)methyl, trityl, methoxymethyl, 1-ethoxyethyl or methylthiomethyl, or 2-oxa- or 2-thia-cycloalkyl having from 5 to 7 ring atoms, for example 2-tetrahydrofuryl or 2 -tetrahydropyranyl, $R^3$ represents hydroxy or protected hydroxy, for example tri-lower alkylsilyloxy, for example trimethylsilyloxy, tert-butyldimethylsilyloxy or 1,1,2-trimethylpropyl-dimethylsilyl-oxy, aryl-substituted silyloxy, for example dimethylphenylsilyloxy or triphenylsilyloxy, lower alkoxy that is substituted and/or branched in the 1-position, for example tert-butoxy, diphenylmethoxy, di(p-methoxyphenyl)methoxy, trityloxy, methoxymethoxy, 1-ethoxyethoxy or methylthiomethoxy, or 2-oxa- or 2-thia-cycloalkoxy having from 5 to 7 ring atoms, for example 2-tetrahydrofuryloxy or 2-tetrahydropyranyloxy, $R^4$ represents hydrogen or a carboxy-protecting group, for example a carboxy-protecting group mentioned under $R^2$, or $R^3$ and $R^4$ together represent a bond, and $Z^2$ represents amino or acylamino, for example unsubstituted or substituted lower alkanoylamino, for example formylamino, acetylamino, propionylamino, tert-butylcarbonylamino, chloroacetylamino, trichloroacetylamino or trifluoroacetylamino, lower alkoxycarbonylamino, for example tert-butoxycarbonylamino, aryl-lower alkoxycarbonylamino, for example benzyloxycarbonylamino, 4-nitrobenzyloxycarbonylamino or diphenylmethoxycarbonylamino, or arylcarbonylamino, for example benzoylamino, the pure diastereoisomers thereof and salts thereof.

The invention relates especially to pure diastereoisomers of the compounds of formula III in which $R^2$ represents hydrogen, lower alkyl, for example methyl or ethyl, or a carboxy-protecting group, for example tri-lower alkylsilyl, for example trimethylsilyl, $R^3$ represents hydroxy or protected hydroxy, for example tri-lower alkylsilyloxy, for example trimethylsilyloxy, $R^4$ represents hydrogen or a carboxy-protecting group, for example tri-lower alkylsilyl, for example trimethylsilyl, or $R^3$ and $R^4$ together represent a bond, and $Z^2$ represents amino, lower alkanoylamino, for example acetylamino or tert-butylcarbonylamino, lower alkoxycarbonylamino, for example tert-butoxycarbonylamino, or arylcarbonylamino, for example benzoylamino, and salts thereof.

The invention relates chiefly to the (2S,3S,4R)-, (2R,3R, 4S)-, (2R,3S,4S)-, (2S,3R,4R)-, (2R,3S,4R)- and (2S,3R,4S) -diastereoisomers of the compounds of formula III in which $R^2$ represents hydrogen, lower alkyl, for example methyl or ethyl, tri-lower alkylsilyl, for example trimethylsilyl, $R^3$ represents hydroxy or tri-lower alkylsilyloxy, for example trimethylsilyloxy, $R^4$ represents hydrogen or tri-lower alkylsilyl, for example trimethylsilyl, or $R^3$ and $R^4$ together represent a bond, and $Z^2$ represents amino or lower alkanoylamino, for example acetylamino or tert-butylcarbonylamino, and salts thereof.

The invention relates especially to the (2S,3S,4R)-, (2R, 3R,4S)-, (2R,3S,4S)- and (2R,3S,4R)-diastereoisomers of the compounds of formula III in which $R^2$ represents hydrogen or lower alkyl, for example methyl or ethyl, $R^3$ and $R^4$ together represent a bond, and $Z^2$ represents amino or lower alkanoylamino, for example acetylamino, and salts thereof.

Similarly, the invention relates to the (2S,3S,4R)-diastereoisomers of the compounds of formula III in which $R^2$ represents hydrogen or lower alkyl, for example methyl or ethyl, $R^3$ represents hydroxy or tri-lower alkylsilyloxy, for example trimethylsilyloxy, $R^4$ represents hydrogen or tri-lower alkylsilyl, for example trimethylsilyl, and $Z^2$ represents amino, and salts thereof.

The invention also relates to the compound of formula IV and its pure diastereoisomers, especially the (3S,4S,1'R)-diastereoisomer.

The invention relates especially to the intermediates mentioned in the Examples.

Starting materials

The invention relates also to novel starting materials and processes for their manufacture. The invention relates especially to pure enantiomers of compounds of the formula II in which $R^1$ represents lower alkyl and $Z^1$ represents hydroxy, etherified hydroxy, esterified hydroxy, amino, arylmethylamino, acylamino or azido, to tautomeric forms of these compounds, for example the compounds of formula IIa in which $R^1$ represents lower alkyl and Y represents oxo, imino, arylmethylimino or acylimino, and to salts of these compounds having salt-forming groups.

Etherified hydroxy $Z^1$ is, for example, unsubstituted or substituted lower alkoxy, for example lower alkoxy, for example methoxy or ethoxy, lower alkoxy-lower alkoxy, for example 1- or 2-methoxyethoxy or -ethoxyethoxy or methoxymethoxy, lower alkanoyloxy-lower alkoxy, for example acetoxymethoxy or tert-butylcarbonyloxymethoxy, or aryl-lower alkoxy, for example benzyloxy or 2-phenylethoxy, aryloxy, for example phenoxy, or silyloxy, for example tri-lower alkylsilyloxy, for example trimethylsilyloxy or tert-butyldimethylsilyloxy, or triarylsilyloxy, for example triphenylsilyloxy.

Esterified hydroxy $Z^1$ is esterified, for example, with a mineral acid, or organic sulphonic acid or a carboxylic acid and is, for example, halogen, for example chlorine, bromine or iodine, unsubstituted or substituted lower alkanesulphonyloxy, for example methanesulphonyloxy, trifluoromethanesulphonyloxy or camphor-10-sulphonyloxy, arenesulphonyloxy, for example benzenesulphonyloxy, p-toluenesulphonyloxy, p-nitrobenzenesulphonyloxy or 2,4-dinitrobenzenesulphonyloxy, unsubstituted or substituted lower alkanoyloxy, for example formyloxy, acetoxy, propionoxy, tert-butylcarbonyloxy, chloroacetoxy, fluoroacetoxy or trifluoroacetoxy, lower alkoxy-carbonyloxy, for example methoxycarbonyloxy or n- or tert-butoxycarbonyloxy, or arylcarbonyloxy, for example benxoyloxy.

The invention relates especially to pure enantiomers of the compounds of formula II in which $R^1$ represents lower alkyl, for example methyl, ethyl or tert-butyl, and $Z^1$ represents hydroxy, unsubstituted or substituted lower alkoxy, for example unsubstituted lower alkoxy, for example methoxy or ethoxy, lower alkoxy-lower alkoxy, for example 1- or 2-methoxyethoxy or -ethoxyethoxy or methoxymethoxy, lower alkanoyloxy-lower alkoxy, for example acetoxymethoxy or tert-butylcarbonyloxymethoxy, or aryl-lower alkoxy, for example benzyloxy or 2-phenylethoxy, aryloxy, for example phenoxy, silyloxy, for example tri-lower alkylsilyloxy, for example trimethylsilyloxy or tert-butyldimethylsilyloxy, or triarylsilyloxy, for example triphenylsilyloxy, halogen, for example chlorine, bromine or iodine, unsubstituted or substituted lower alkanesulphonyloxy, for example methanesulphonyloxy, trifluoromethanesulphonyloxy or camphor-10-sulphonyloxy, arenesulphonyloxy, for example benzenesulphonyloxy, p-toluenesulphonyloxy, p-nitrobenzenesulphonyloxy or 2,4-dinitrobenzenesulphonyloxy, unsubstituted or substituted lower alkanoyloxy, for example formyloxy, acetoxy, propionoxy, tert-butylcarbonyloxy, chloroacetoxy, fluoroacetoxy or trifluoroacetoxy, lower alkoxycarbonyloxy, for example methoxycarbonyloxy or n- or tert-butoxycarbonyloxy, arylcarbonyloxy, for example benzoyloxy, amino, arylmethylamino, for example benzylamino, dibenzylamino, 2-, 3- or 4-methylbenzylamino, α- or β-naphthylamino or diphenylmethylamino, unsubstituted or substituted lower alkanoylamino, for example formylamino, acetylamino, propionylamino, tert-butylcarbonylamino, chloroacetylamino, trichloroacetylamino or trifluoroacetylamino, lower alkoxycarbonylamino, for example tert-butoxycarbonylamino, aryl-lower alkoxycarbonylamino, for example benzyloxycarbonylamino, 4-nitrobenzyloxycarbonylamino or diphenylmethoxycarbonylamino, arylcarbonylamino, for example benzoylamino, or azido, to tautomeric forms of these compounds, for example the compounds of formula IIa in which $R^1$ represents lower alkyl and Y represents oxo, imino, arylmethylimino or acylimino, and to salts of these compounds having salt-forming groups.

The invention relates chiefly to pure enantiomers of compounds of the formula II in which $R^1$ represents lower alkyl, for example methyl, ethyl or tert-butyl, and $Z^1$ represents hydroxy, halogen, for example chlorine, bromine or iodine, unsubstituted or substituted lower alkanesulphonyloxy, for example methanesulphonyloxy, trifluoromethanesulphonyloxy or camphor-10-sulphonyloxy, arenesulphonyloxy, for example benzenesulphonyloxy, p-toluenesulphonyloxy, p-nitrobenzenesulphonyloxy or 2,4-dinitrobenzenesulphonyloxy, amino, arylmethylamino, for example benzylamino or dibenzylamino, lower alkanoylamino, for example acetylamino or tert-butylcarbonylamino, lower alkoxycarbonylamino, for example tert-butoxycarbonylamino, arylcarbonylamino, for example benzoylamino, or azido, to tautomeric forms of these compounds, for example the compounds of formula IIa in which $R^1$ represents lower alkyl and Y represents oxo, imino, arylmethylimino or acylimino, and to salts of these compounds having salt-forming groups.

The invention relates especially to pure enantiomers of the compounds of formula II in which $R^1$ represents lower alkyl, for example methyl, ethyl or tert-butyl, and $Z^1$ represents hydroxy, lower alkanesulphonyloxy, for example methanesulphonyloxy, camphorsulphonyloxy, for example d-camphor-10-sulphonyloxy, arenesulphonyloxy, for example p-toluenesulphonyloxy, p-nitrobenzenesulphonyloxy or 2,4-dinitrobenzenesulphonyloxy, amino, arylmethylamino, for example benzylamino, lower alkanoylamino, for example acetylamino, or azido, to tautomeric forms of these compounds, for example the compounds of formula IIa in which $R^1$ represents lower alkyl and Y represents oxo, imino, arylmethylimino or lower alkanoylimino, and to salts of these compounds having salt-forming groups.

The novel compounds of formula II according to the invention and their salts are manufactured according to processes known per se, for example as follows:

a) an enantiomerically pure compound of the formula

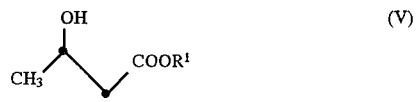

in which $R^1$ represents lower alkyl is condensed with an oxalic acid diester, or b) a racemic compound of the formula II in which $R^1$ represents lower alkyl and $Z^1$ represents hydroxy, amino or arylmethylamino, is reacted with an enantiomerically pure chiral acid or a reactive derivative thereof, the resulting diastereoisomeric mixture is separated into the diastereoisomers and, if desired, the pure diastereoisomers are cleaved again, or c) in a prochiral compound of the formula

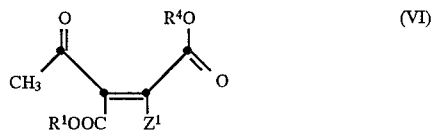

in which $R^1$ represents lower alkyl and $R^4$ represents hydrogen or a carboxy-protecting group and $Z^1$ is as defined under formula II, the carbonyl group is reduced with a chiral reducing agent and, if applicable, after removing the protecting group $R^4$, the lactone ring is closed with an acid and, if desired, a resulting enantiomerically pure compound of the formula II is converted into a different enantiomerically pure compound of the formula II and/or a resulting salt is converted into the free compound or into a different salt or a resulting free compound is converted into a salt.

The condensation in process a) is carried out under the customary reaction conditions of a ester crosscondensation. The hydroxybutyric acid ester is deprotonated with two or more equivalents of a strong non-nucleophilic base and the dianion formed is reacted with the oxalic acid ester in a polar, preferably aprotic, solvent.

Suitable non-nucleophilic bases are, for example, alkali metal amides, for example lithium diisopropylamide, lithium cyclohexylethylamide, lithium 2,2,6,6-tetramethylpiperidide or lithium, sodium or potassium bis(trimethylsilyl)amide, branched alkyllithium compounds, for example tert-butyllithium, or alkali metal hydrides, for example sodium or potassium hydride.

Suitable polar aprotic solvents are, for example, ethers, for example tetrahydrofuran or dimethoxyethane, amides, for example dimethylformamide, N-methylpyrrolidone or hexamethylphosphoric acid triamide, dimethyl sulphoxide, cyclic ureas, for example N,N'-dimethyl-N,N'-propyleneurea, or also mixtures of the said solvents with each other and/or with hydrocarbons, for example n-pentane, n-hexane or cyclohexane. It is also possible to use lower alkanols as solvents, for example the alcohol $R^1OH$, for example methanol, ethanol or tert-butanol, there then being used as bases the corresponding alkali metal alcholates, for example sodium methanolate or potassium tert-butanolate.

The condensation reaction is carried out preferably at low temperatures, for example of from −100° C. to 0° C., for example from −78° C. to −30° C., if desired under a protective gas atmosphere, for example nitrogen or argon.

In process b), for example a racemic compound of the formula II in which $Z^1$ represents amino or arylmethylamino, for example benzylamino, is converted with an enantiomerically pure chiral acid into a mixture of two diastereoisomeric acid addition salts. Suitable acids are, for example, chiral carboxylic acids, for example tartaric acid, diacetyltartaric acid, malic acid, glutamic acid, pyrrolidone-5-carboxylic acid (pyroglutamic acid) or menthoxyacetic acid, and also chiral sulphonic acids, for example camphor-10-sulphonic acid. The diastereoisomeric salts obtainable are cleaved by customary physical methods, for example by fractional cyrstallisation. The diastereoisomerically pure salts can be cleaved again into the enantiomerically pure compounds of formula II in customary manner. for example by treatment with a base or with an ion exchanger.

Racemic compounds of the formula II in which $Z^1$ represents hydroxy are esterified by an enantiomerically pure chiral acid or a suitable derivative of such an acid. The esterification with one of the mentioned chiral carboxylic acids is carried out under customary conditions, for example in the presence of an anhydrous mineral acid, an organic sulphonic acid or a Lewis acid, as described hereinbefore in the conversion of compounds of the formula III one into another. Preferably, however, derivatives of the mentioned chiral carboxylic or sulphonic acids, for example anhydrides, for example symmetrical carboxylic acid anhydrides, or halides, for example acid chlorides, are used for the esterification. The esterification with an acid chloride, for example pyroglutamic acid chloride, menthoxyacetic acid chloride or, especially, camphor-10-sulphonic acid chloride, is carried out in an inert solvent, for example toluene, diethyl ether or methylene chloride, in the presence of a base, for example a tertiary amine, for example triethylamine or N-methylmorpholine, or an alkali metal or alkaline earth metal carbonate, for example sodium, potassium or calcium carbonate, at temperatures of from −30° C. to 50° C., preferably at approximately 0° C. The diastereoisomeric esters obtainable are separated by customary physical methods, for example by fractional crystallisation or by column chromatography. The diastereoisomerically pure esters obtainable are enantiomerically pure compounds of the formula II in which $Z^1$ represents chirally esterified hydroxy. If desired, they can be cleaved again according to the customary methods of ester hydrolysis into enantiomerically pure compounds of the formula II in which $Z^1$ represents hydroxy.

Racemic compounds of the formula II in which $Z^2$ represents hydroxy can also be esterified by an anhydride of a diacid, for example phthalic acid, succinic acid or maleic acid anhydride, and the acids obtainable can be converted by salt formation with enantiomerically pure chiral amines, for example α-phenethylamine, brucine or abietylamine, into mixtures of diastereoisomeric salts, which can be separated by crystallisation. Cleavage according to customary methods yields enantiomerically pure compounds of the formula II.

Racemic compounds of the formula II in which $Z^1$ represents amino or arylmethylamino can be acylated at the amino group in the manner described hereinbefore. If the acylation agents used are derivatives of enantiomerically pure chiral acids, for example of the above-mentioned carboxylic or sulphonic acids, then mixtures of diastereoisomeric amides are formed that can be separated by fractional crystallisation or by chromatography. The diastereoisomerically pure amides obtainable are enantiomerically pure compounds of the formula II in which $Z^1$ represents chiral acylamino.

Suitable chiral reducing agents for process c) are, for example, enantiomerically pure chiral boranes that contain a transferable hydrogen atom, for example (+)- or (−)- diisopinocampheylborane, or lithium aluminium hydride in the presence of enantiomerically pure chiral alcohols, aminoalcohols or amines, for example 1,1'-di(β-naphthol), Darvon alcohol or 2,6-dimethyl-N-(2-pyrrolidinylmethyl) aniline. Suitable solvents are the solvents customarily used in hydroborations or hydride reductions, for example anhydrous ethers, for example diethyl ether, tetrahydrofuran or 1,2-dimethoxyethane. Preferably, the reductions are carried out at low temperatures, for example at from −100° C. to 0° C., for example at approximately −30° C.

The hydroxy compound obtainable from the reduction, if applicable, after removal of the protecting group $R^4$, is cyclised with an acid to form the lactone of formula II in the manner described hereinbefore. Suitable acids and reaction conditions are mentioned hereinbefore under the esterification of compounds of the formula III, but for the lactone ring formation the alcohol of the formula $R^2OH$ is omitted.

Compounds of the formula II in which $Z^1$ represents hydroxy, etherified hydroxy or esterified hydroxy are converted according to methods known per se into compounds of the formula II in which $Z^1$ represents amino, arylmethylamino, acylamino or azido. For example, the hydroxy group is converted into a reactive leaving group, for example a halide, for example a chloride, or a sulphonate, for example a lower alkanesulphonate, for example mesylate, or an arenesulphonate, for example benzenesulphonate, p-toluenesulphonate, p-nitrobenzenesulphonate or 2,4-dinitrobenzenesulphonate, and this reactive leaving group is replaced by an arylmethylamine, for example a benzylamine or dibenzylamine, or by azide. A compound of the formula II in which $Z^1$ represents etherified or esterified hydroxy is beforehand converted according to customary ether or ester cleaving methods, for example with an acid or base, into a compound in which $Z^1$ represents hydroxy, unless the etherified or esterified hydroxy group is itself a reactive leaving group that may be replaced by azide or by an arylmethylamine, for example 2,4-dinitrophenoxy, halogen, for example chlorine, bromine or iodine, lower alkanesulphonyloxy, for example mesyloxy or camphor-10-sulphonyloxy, or arenesulphonyloxy, for example benzenesulphonyloxy, p-toluenesulphonyloxy, p-nitrobenzenesulphonyloxy or 2,4-dinitrobenzenesulphonyloxy.

The conversion of hydroxy into halogen is carried out with customary halogenating agents, for example phosphorus tri- or penta-halide, for example phosphorus tri- or penta-chloride, phosphorus tribromide or phosphorus oxychloride, triphenylphosphorus dihalide, for example triphenylphosphorus dichloride, or thionyl chloride, in an inert solvent, for example diethyl ether, toluene, dioxane or dimethylformamide, or in an excess of the reagent, optionally in the presence of a base, for example pyridine, at temperatures of from −30° C. to 50° C., for example from 0° C. to room temperature. The conversion of hydroxy into a sulphonate is carried out preferably with the corresponding sulphonic acid halide, for example sulphonic acid chloride, in an inert solvent, for example toluene, diethyl ether or methylene chloride, in the presence of a base, for example a tertiary amine, for example triethylamine or N-methylmorpholine, or an alkali metal or alkaline earth metal carbonate, for example sodium, potassium or calcium carbonate, at temperatures of from −30° C. to 50° C., preferably at approximately 0° C.

Compounds of the formula II in which $Z^1$ represents one of the abovementioned leaving groups are reacted with an arylmethylamine, for example benzylamine, dibenzylamine, 2-, 3- or 4-methylbenzylamine, α- or β-naphthylmethylamine or diphenylmethylamine, or with an alkali metal azide, for example sodium or potassium azide, in a polar solvent, for example water, an alcohol, for example methanol or ethanol, acetic acid, acetone, acetonitrile, dimethylformamide or dimethyl sulphoxide or mixtures thereof, at temperatures of from 0° C. to 50° C., preferably at approximately room temperature. The reaction with arylmethylamine can also be carried out without solvents in an excess of the reagent or in only slightly polar solvents, for example methylene chloride or toluene.

Enantiomerically pure compounds of the formula V, for example (S)- or (R)-3-hydroxybutyric acid esters, are known or can be produced according to known methods, for example by esterification of the hydroxy acid obtainable by depolymerisation of polyhydroxybutyric acid.

Racemic compounds of the formula II are known or can be produced from the known racemic compound of formula II in which $R^1$ represents ethyl and $Z^1$ represents hydroxy according to one of the methods described hereinbefore for the conversion of compounds of the formula II or III.

Compounds of the formula VI are known or can be produced according to known methods, for example by ester crosscondensation of acetoacetic acid ester with oxalic acid ester or of acetic acid ester with oxaloacetic acid ester analogously to the process described in process a).

The following Examples serve to illustrate the invention but do not limit the scope thereof in any way.

The values for proton nuclear resonance spectroscopy ($^1$H-NMR) are given in ppm (parts per million) based on tetramethylsilane (δ=0) as an internal standard. s=singlet, d=doublet, t=triplet, q=quartet, m=multiplet, dxd=double doublet. Optical rotations $[\alpha]_D$ are, unless indicated otherwise, measured at the sodium-D-line, concentration in g per 100 ml.

EXAMPLE 1

(R)-2-hydroxy-3-methoxycarbonyl-2-penten-4-olide 775 ml of 1.6M n-butyllithium solution in n-hexane are added dropwise within a period of 20 minutes at −25° C. to a solution of 1.27 mol of diisopropylamine in 600 ml of tetrahydrofuran. At −70° C., 70.9 g of (R)-3-hydroxybutyric acid methyl ester are then added dropwise within a period of 30 minutes and, after 1 hour, 70.9 g of oxalic acid dimethyl ester are added dropwise within a period of 40 minutes. After a reaction time of two hours at −60° C., the whole is warmed to 0° C. and acidified to pH 2 with 430 ml of 6N hydrochloric acid. The product is isolated by repeated extraction with ethyl acetate and pre-purified by extraction into aqueous bicarbonate solution, acidification with 6N hydrochloric acid to pH 2.5 and extraction once more with ethyl acetate. The solvent is distilled off and the residue is recrystallised from ether/petroleum ether. $[\alpha]_D^{20}$=+30.0° (3% in CHCl$_3$), m.p. 94°–96° C.

EXAMPLE 2

The following are manufactured analogously to Example 1:

a) (R)-2-hydroxy-3-ethoxycarbonyl-2-penten-4-olide, $[\alpha]_D^{20}$=+25.0° (3% in CHCl$_3$), m.p. 56°–57° C., from (R)-3-hydroxybutyric acid ethyl ester;

b) (S)-2-hydroxy-3-methoxycarbonyl-2-penten-4-olide, $[\alpha]_D^{20}$=−30° (3% in CHCl$_3$), m.p. 94°–96° C., from (S)-3-hydroxybutyric acid methyl ester.

EXAMPLE 3

(R)- and (S)-2-(d-camphor-10-sulphonyloxy)-3-ethoxycarbonyl-2-penten-4-olide 52.1 g of racemic 2-hydroxy-3-ethoxycarbonyl-2-penten-4-olide (manufactured according to A. Rossi and H. Schinz, Helv. Chim. Acta 31, 473 (1948)) and 87.8 g of d(+)-camphor-10-sulphonyl chloride are dissolved in 280 ml of toluene and the solution is reacted at −10° C. with 33.4 g of triethylamine. The solution is acidified, washed until neutral, filtered over silica gel and concentrated by evaporation. The orange-red oil is crystallised from ethyl acetate/cyclohexane by fractional crystallisation. The (S)/d-camphorsulphonyl derivative crystallises first, whilst the (R)/d-camphorsulphonyl derivative becomes concentrated in the mother liquor. The (R)/d-camphorsulphonyl derivative, too, is obtained in crystalline form by repeated fractionation.

(S)/d-camphorsulphonyl derivative: $[\alpha]_D^{20}=-11°$ (3% in $CHCl_3$), m.p. 114°–115° C., IR 1765, 1730, 1710 $cm^{-1}$.

(R)/d-camphorsulphonyl derivative: $[\alpha]_D^{20}=+16°$ (3% in $CHCl_3$), m.p. 75°–77° C., IR 1765, 1730, 1710 $cm^{-1}$.

EXAMPLE 4

(R)-2-mesyloxy-3-methoxycarbonyl-2-penten-4-olide 137.76 g of (R)-2-hydroxy-3-methoxycarbonyl-2-penten-4-olide are dissolved in 660 ml of toluene and at −10° C. 110 g of methanesulphonyl chloride and then, within a period of 1 hour, 97 g of triethylamine, are added. 350 ml of water and 150 ml of saturated sodium chloride solution are added, the toluene product phase is removed and the aqueous phase is re-extracted twice with 250 ml of toluene. The toluene phases are washed with sodium chloride solution and with water and concentrated by evaporation. Orange-red oil, $[\alpha]_D^{20}=+10.6°$ (3% in $CHCl_3$).

EXAMPLE 5

(R)-2-(2,4-dinitrobenzenesulphonyloxy)-3-ethoxycarbonyl-2-penten-4-olide

The title compound is manufactured analogously to Example 4 from 2,4-dinitrobenzenesulphonyl chloride and (R)-2-hydroxy-3-ethoxycarbonyl-2-penten-4-olide, $[\alpha]_D^{20}=-17°$ (3% in $CHCl_3$), m.p. 95°–96° C.

EXAMPLE 6

(R)-2-(4-nitrobenzenesulphonyloxy)-3-methoxycarbonyl-2penten-4-olide 34.44 g of (R)-2-hydroxy-3-methoxycarbonyl-2-penten-4-olide are dissolved in 170 ml of toluene at 40° C., 49.4 g of p-nitrobenzenesulphonyl chloride in 160 ml of toluene are added and the whole is cooled to 5° C. Within a period of 30 minutes, 20.3 g of N-methylmorpholine are metered in at from 0° to 5° C. 350 ml of water are added, the toluene product phase is removed, and the aqueous phase is re-extracted twice with 100 ml of toluene. The toluene phases are washed with sodium chloride solution and with water, filtered over a small amount of silica gel and concentrated by evaporation. The residue is crystallised from ethyl acetate/cyclohexane. $[\alpha]_D^{20}=+12.4°$ (3% in $CHCl_3$), m.p. 123°–124° C.

EXAMPLE 7

(R)-2-benzylamino-3-methoxycarbonyl-2-penten-4-olide

At 0° C., 25.5 g of benzylamine are added dropwise within a period of 1 hour to a solution of 35.7 g of (R)-2-(4-nitrobenzenesulphonyloxy)-3-methoxycarbonyl-2-penten-4-olide in 250 ml of methylene chloride. The resulting benzylamine-p-nitrobenzenesulphonic acid salt is filtered off, and the filtrate is concentrated by evaporation, filtered over silica gel with toluene, and recrystallised from ether/petroleum ether. $[\alpha]_D^{20}=+22°$ (3% in $CHCl_3$), m.p. 68°–70° C., IR ($CH_2Cl_2$) 1752, 1678, 1632 $cm^{-1}$.

EXAMPLE 8

(R)-2-azido-3-methoxycarbonyl-2-penten-4-olide

A solution of 62 g of sodium azide in 180 ml of water is added dropwise within a period of 1 hour at 20° C. to a solution of 190.4 g of (R)-2-mesyloxy-3-methoxycarbonyl-2-penten-4-olide in 275 ml of acetone and 55 ml of glacial acetic acid in such a manner that the internal temperature does not exceed 25° C. After 4 hours at 25° C., 500 ml of water and 500 ml of toluene are mixed in by stirring. The toluene phase is separated off, and the aqueous phase is freed of acetone in a rotary evaporator and repeatedly extracted with toluene. The toluene extracts are dried and concentrated in vacuo to an approximately 30% solution. A sample is concentrated by evaporation: oil, $[\alpha]_D^{20}=+8°$ (3% in $CH_3CN$), IR 2110 $cm^{-1}$.

The title compound can be produced in an analogous manner also from the corresponding (R)-2-(2,4-dinitrobenzenesulphonyloxy)-, 2-(4-nitrobenzenesulphonyloxy)- or 2-(d-camphor-10-sulphonyloxy)-3-methoxycarbonyl-2-penten-4-olides.

EXAMPLE 9

(R)-2-amino-3-methoxycarbonyl-2-penten-4-olide by reduction of the azide

The approximately 30% toluene solution containing 0.75 mol of (R)-2-azido-3-methoxycarbonyl-2-penten-4-olide of Example 8 is diluted with 1.0 l of ethyl acetate, 22 g of Pd/C (5%) are added and the whole is hydrogenated at 20°–25° C. at normal pressure for 3–4 hours. The catalyst is filtered off, the solvent is distilled off, and the residue is recrystallised from ethyl acetate/n-heptane. $[\alpha]_D^{20}=+30.9°$ (3% in $CHCl_3$), m.p. 106°–108° C.

EXAMPLE 10

The following are produced analogously to Examples 8 and 9 starting from the camphor sulphonates of Example 3 and via the corresponding azide:

a) (R)-2-amino-3-ethoxycarbonyl-2-penten-4-olide, $[\alpha]_D^{20}=+25.1°$.

b) (S)-2-amino-3-ethoxycarbonyl-2-penten-4-olide, $[\alpha]_D^{20}=-24.5°$.

EXAMPLE 11

(R)-2-amino-3-methoxycarbonyl-2-penten-4-olide by hydrogenation of the benzylamine 3 g of (R)-2-benzylamino-3-methoxycarbonyl-2-penten-4-olide are dissolved in 30 ml of ethanol, 0.3 g of Pd/C (5%) is added, the whole is diluted with 4 ml of 10% ethanolic hydrochloric acid solution and hydrogenation is carried out at 35° C. and normal pressure until saturation is reached. The catalyst is filtered off, the solvent is distilled off, and the residue is recrystallised from ethyl acetate/cyclohexane. $[\alpha]_D^{20}=+31°$ (3% in $CHCl_3$), m.p. 106°–108° C.

EXAMPLE 12

(R)-2-acetamido-3-ethoxycarbonyl-2-penten-4-olide 12.04 g of (R)-2-amino-3-ethoxycarbonyl-2-penten-4-olide are dissolved in 48 ml of acetic anhydride, 125 mg of toluenesulphonic acid monohydrate are added and the whole is stirred overnight at 40° C. The mixture is concentrated by evaporation, dissolved in ethyl acetate and washed with water. The ethyl acetate is distilled off and the residue is recrystallised from ethyl acetate/cyclohexane, $[\alpha]_D^{20}$=+62.3° (3% in $CHCl_3$), m.p. 119°–122° C.

EXAMPLE 13

The following are produced analogously to Example 12:
a) (R)-2-acetamido-3-methoxycarbonyl-2-penten-4-olide, $[\alpha]_D^{20}$=+61.0° (3% in $CHCl_3$), m.p. 133°–134° C.
b) (S)-2-acetamido-3-ethoxycarbonyl-2-penten-4-olide, $[\alpha]_D^{20}$=−63.0° (3% in $CHCl_3$), m.p. 121°–122° C.

EXAMPLE 14

2(S)-acetamido-3(S)-methoxycarbonyl-4(R)-pentanolide 169.2 g of (R)-2-acetamido-3-methoxycarbonyl-2-penten-4-olide are dissolved in 800 ml of methanol, 10 g of Pd/C (5%) are added and the whole is hydrogenated for 8 hours at 30° C. and 3–5 bars. The catalyst is filtered off, washed with methanol and the filtrate is concentrated by evaporation. The ratio of the diastereoisomers of the crude product exhibited by HPLC analysis is (2S,3S,4R):(2R,3S,4R):(2S,3R,4R)=approximately 5:3:2. The proportion of the (2R,3R,4R)-diastereoisomer is less than 1%. The mixture is dissolved in 500 ml of methanol, 12 g of 1,8-diazabicyclo[5.4.0]undec-7-ene are added and the whole is stirred at room temperature for 48 hours, resulting in a mixture, 86–88% of which consists of the desired (2S,3S,4R)-diastereoisomer. The solution is concentrated, neutralised with 2N hydrochloric acid, taken up in ethyl acetate and extracted with saturated sodium chloride solution. Diastereoisomerically pure title compound is obtained by crystallisation from ethyl acetate/cyclohexane, $[\alpha]_D^{20}$=−49.5° (3% in $CH_3OH$), m.p. 105°–106° C., IR 1787, 1740, 1689, 1510 $cm^{-1}$.

The (2R,3S,4R)- and the (2S,3R,4R)-diastereoisomers can be isolated in pure form from the crude product by preparative HPLC.

EXAMPLE 15

2(R)-acetamido-3(S)-ethoxycarbonyl-4(S)-pentanolide 0.45 g of rhodium/$Al_2O_3$ catalyst is added to 1.5 g of (S)-2-acetamido-3-ethoxycarbonyl-2-penten-4-olide dissolved in 100 ml of ethyl acetate and the whole is hydrogenated at 50° C. and 50 bars for 21 hours and worked up as in Example 14. The ratio of the diastereoisomers of the crude product exhibited by HPLC analysis is (2R,3S,4S):(2S,3R,4S):(2R,3R,4S)=approximately 85:13:2. Diastereoisomerically pure title compound is obtained by crystallisation from ethyl acetate, $[\alpha]_D^{20}$=−183.2° (3% in $CHCl_3$), m.p. 165°–167° C.

The same diastereoisomer can also be manufactured by using Nishimura catalyst (Pt/Rh) instead of Rh on $Al_2O_3$.

EXAMPLE 16

2(S)-amino-3(S)-carboxy-4(R)-pentanolide 114.4 g of 2(S)-acetamido-3(S)-methoxycarbonyl-4(R)-pentanolide are heated at 120° C. for 24 hours in semi-concentrated hydrochloric acid. The solution is slowly cooled to 0° C., and the precipitate is filtered off, washed with ethyl acetate, dried under a high vacuum and recrystallised from methanol. Hydrochloride of the title compound, $[\alpha]_D^{20}$=−21.5° (1% in $H_2O$), m.p. >250° C. The free title compound is obtained by treating the hydrochloride with an excess of propylene oxide in hot methanol, $[\alpha]_D^{20}$=−23.1° (1% in 1N HCl), m.p. 196°–200° C.

EXAMPLE 17

2(R)-amino-3(R)-carboxy-4(S)-pentanolide

The title compound is obtained analogously to Example 14 and 16 from (S)-2-acetamido-3-ethoxycarbonyl-2-penten-4-olide. $[\alpha]_D^{20}$=+22.5° (1% in 1N HCl), m.p. 200°–204° C.

EXAMPLE 18

2(S)-amino-3(S)-methoxycarbonyl-4(R)-pentanolide hydrochloride 19.56 g of 2(S)-amino-3(S)-carboxy-4(R)-pentanolide hydrochloride are suspended in methanol, the whole is gassed with hydrogen chloride for 15 minutes and stirred overnight at room temperature. The solvent is distilled off in a rotary evaporator and the residue is crystallised from chloroform: $[\alpha]_D^{20}$=−27.3° (1% in DMSO), m.p. 170°–172° C.

EXAMPLE 19

The following are manufactured analogously to Example 18:
a) 2(R)-amino-3(R)-methoxycarbonyl-4(S)-pentanolide hydrochloride, $[\alpha]_D^{20}$=+26.7° (1% in DMSO), m.p. 171°–172° C.
b) 2(S)-amino-3(S)-ethoxycarbonyl-4(R)-pentanolide hydrochloride, produced in ethanol instead of in methanol, $[\alpha]_D^{20}$=−29.6° (3% in $CHCl_3$), amorphous.

EXAMPLE 20

2(S)-amino-3(R)-methoxycarbonyl-4(R)-pentanolide hydrochloride 4.28 g of (R)-2-amino-3-methoxycarbonyl-2-penten-4-olide (Example 9) are dissolved in 45 ml of approximately 0.6M HCl in methanol and hydrogenated for 7 hours in the presence of 1 g of rhodium on Alox (5%) at 60°–65° C. and approximately 50 bars. The catalyst is filtered off and washed with methanol. The filtrate is concentrated by evaporation and the residue is crystallised from chloroform/cyclohexane. $[\alpha]_D^{20}$=+113.4° (1% in DMSO), m.p. 178°–179° C. $^1$H-NMR (DMSO): 1.26 (3H, d 6.4 Hz), 3.69 (3H, s), 3.74 (1H, dxd 7.2 and 5.3 Hz), 4.77 (1H, d 7.2 Hz), 4.92 (1H, dxq 6.4 and 5.3 Hz), 9.1 (3H, broad, $NH_3^+$).

The title compound is epimerised by 1,8-diazabicyclo[5.4.0]undec-7-ene in methanol analogously to Example 14 to the (2S,3S,4R)-diastereoisomer (Example 18) and crystallised in the form of a hydrochloride from chloroform: $[\alpha]_D^{20}$=−27.3° (1% in DMSO), m.p. 170°–172° C.

EXAMPLE 21

2(S)-amino-3(S)-carboxy-4(R)-hydroxypentanoic acid (β(S)-(1'(R)-hydroxyethyl)-L-aspartic acid)

2.07 g of 2(S)-amino-3(S)-carboxy-4(R)-pentanolide are suspended in 10 ml of methanol and dissolved by the addition of 13 ml of 2N aqueous sodium hydroxide solution with stirring at room temperature. The solvent mixture is distilled off and acetonitrile is added to the oily residue. The crystals which gradually form are filtered off, washed with a small amount of acetonitrile and dried under a high vacuum. The disodium salt of the title compound remains behind, $[\alpha]_D^{20}$=−9.0° (1% in water). $^1$H-NMR ($D_2O$): 1.21 (3H, d 6.4 Hz), 2.54 (1H, dxd 6.4 and 8.4 Hz), 3.49 (1H, d 6 Hz), 3.97 (1H, dxq 8.4 and 6.4 Hz).

The free acid is obtained by dissolving the disodium salt in an equivalent amount of 1N hydrochloric acid.

EXAMPLE 22

2(S)-amino-3(S)-ethoxycarbonyl-4(R)-hydroxy-pentanoic acid 56.0 g of 2(S)-amino-3(S)-ethoxycarbonyl-4(R)-pentanolide hydrochloride are dissolved in methylene chloride and the pH is adjusted to 7.5 with sodium bicarbonate solution. The methylene chloride phase is separated off, the aqueous phase is saturated with sodium chloride and extracted repeatedly with methylene chloride, and the organic phases are concentrated by evaporation. 106 ml of 2N sodium hydroxide solution are added dropwise to the residue in 120 ml of ethanol at 0° C. within a period of 6 hours. The solution is then concentrated to half its volume, adjusted to pH 3.9 with 103 ml of 2N hydrochloric acid, and completely concentrated by evaporation. The residue is crystallised from isopropanol/diisopropyl ether, stirred up with methanol and filtered over silica gel. $[\alpha]_{365}^{20}=+14.5°$ (1% in $H_2O$), m.p. 150°–151° C.

EXAMPLE 23

3(S)-(1'(R)-hydroxyethyl)-2-azetidinone-4(S)-carboxylic acid 7.9 g of 2(S)-amino-3-(S)-ethoxycarbonyl-4(R)-hydroxy-pentanoic acid are suspended in 40 ml of toluene, 9.5 ml of hexamethyldisilazane and 2.85 ml of trimethylchlorosilane are added, and then the whole is refluxed overnight. After cooling, with the exclusion of moisture and under an argon atmosphere, precipitated ammonium chloride is filtered off and the toluene is distilled off. Approximately 1 g of ammonia gas is introduced into the oily residue, which is stirred overnight at room temperature and degassed. The bis-silyl compound of the starting material remains behind in the form of a colourless oil. B.p. 110° C./0.01 mbar, $[\alpha]_D^{20}=-11.8°$ (3% in $CH_2Cl_2$).

A solution of 7.75 g of the above bis-silyl compound in 20 ml of absolute tetrahydrofuran is added dropwise at −5° C. within a period of 30 minutes to a tert-butylmagnesium chloride solution in tetrahydrofuran (45 ml, 73.2 mmol). The whole is then stirred at room temperature for 4 hours. The mixture is carefully hydrolysed at 0° C. with 10 ml of water and acidified to pH 4.0 with dilute phosphoric acid. The tetrahydrofuran is distilled off, precipitated magnesium hydrogen phosphate is filtered off, and the clear aqueous solution is concentrated, adjusted to pH 2.8 with phosphoric acid and then to pH 4.5 with 5M ammonia solution, and filtered again. The filtrate is concentrated by evaporation and the residue is chromatographed on silica gel. The product is crystallised from methanol, isopropanol and acetone. IR (DMSO): 1759, 1724 $cm^{-1}$.

Sodium salt, $[\alpha]_{436}^{20}=-3.8°$ (0.45% in DMSO), IR (DMSO): 1747, 1616, 1426 $cm^{-1}$, $^1$H-NMR (DMSO): 1.14 (3H, d 6.2 Hz), 2.86 (1H, m), 3.71 (1H, d 2.5 Hz), 3.89 (1H, m), 5.08 (1H, broad, OH), 7.9 (1H, s, NH).

EXAMPLE 24

4(R)-acetoxy-3(R)-(1'(R)-hydroxyethyl)-2-azetidinone

Instead of the reaction mixture of Example 23 being hydrolysed with water and phosphoric acid it is concentrated to dryness by evaporation. 3.05 g of this crude product, of which approximately 50% is 3(S)-(1'(R)-hydroxyethyl)-2-azetidinone-4(S)-carboxylic acid, are dissolved in 40 ml of glacial acetic acid and 5 ml of triethylamine (water content 0.5%) and electrolysed in a mono-cell at a current density of 40 $mA/cm^2$ and a temperature of 30° C. using platinum electrodes. The content of product formed during the electrolysis is followed by polarography. After a current throughput of approximately 5 Faradays per mol, the mixture is taken up in toluene and concentrated by evaporation in a rotary evaporator at below 45° C. The oil that remains behind is filtered over silica gel with methylene chloride to remove salts and by-products, and recrystallised from toluene, $[\alpha]_D^{20}=+63°$ (1% in $CHCl_3$), m.p. 108°–110° C., $R_f$ (ethyl acetate)=0.45. The crude product contains in addition to the desired (3R, 4R, 1'R)-diastereoisomer approximately 10% of the (3R, 4S,1'R)-diastereoisomer (that is to say the cis-form), $R_f$ (ethyl acetate)=0.35.

EXAMPLE 25

4(R)-(N-allyloxycarbonylglycylthio)-3(S)-(1'(R)-hydroxyethyl)-2-azetidinone

A solution of 426 mg of N-allyloxycarbonyl-thioglycine-dicyclohexylammonium salt in 1.2 ml of 1N aqueous sodium hydroxide solution is washed three times with 1.5 ml of $CH_2Cl_2$ and adjusted to pH 8–9 with 0.1N hydrochloric acid. The resulting aqueous thiolic acid solution is allowed to flow at 25° C. into a solution of 173.2 mg of 4(R)-acetoxy-3(R)-(1'(R)-hydroxyethyl)-2-azetidinone in 1.7 ml of acetonitrile. After the addition of 0.1 ml of 0.1N aqueous sodium hydroxide solution the whole is further stirred for 35 minutes at 21°–23° C. For working up, 250 ml of ethyl acetate and 30 g of NaCl are placed in a separating funnel and the reaction mixture is added thereto. After shaking well and after the removal of the aqueous phase, the organic phase is then washed with 50 ml of 5% aqueous $NaHCO_3$ solution and twice with 50 ml of brine and dried over sodium sulphate. The solvent is removed in a rotary evaporator. The title compound is obtained in the form of an amorphous powder. The crude product can be purified by chromatography on silica gel (toluene/ethyl acetate 2:3). $R_f$ value 0.23 (Merck pre-coated plates, toluene/ethyl acetate=1:4, ninhydrin as development reagent).

We claim:

1. A diastereoisomerically pure (3S,4S,1'R)-diastereoisomer of a compound having the formula

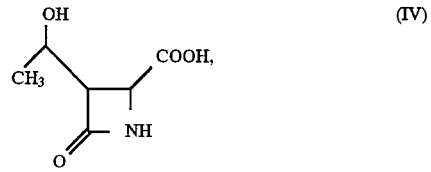

(IV)

and the salts thereof.

* * * * *